(12) United States Patent
Boehl et al.

(10) Patent No.: US 9,097,629 B2
(45) Date of Patent: Aug. 4, 2015

(54) TISSUE CASSETTE WITH RETRACTABLE MEMBER

(71) Applicant: LEICA BIOSYSTEMS NUSSLOCH GMBH, NuBloch (DE)

(72) Inventors: Florian Boehl, Neckargemund (DE); Stella Knorr, Brighton (AU); Peter Kotlarski, Glen Waverley (AU); Graeme Robertson, Ferntree Gully (AU); Chris Ryan, East Brunswick (AU); Ian Sohn, Glen Iris (AU); Wilfred Bauwens, Lilydale (AU); Fernando Dias, Endeavour Hills (AU)

(73) Assignee: Leica Biosystems Nussloch GmbH, NuBloch (DE)

( * ) Notice: Subject to any disclaimer, the term of this patent is extended or adjusted under 35 U.S.C. 154(b) by 0 days.

(21) Appl. No.: 14/204,587

(22) Filed: Mar. 11, 2014

(65) Prior Publication Data
US 2014/0273084 A1    Sep. 18, 2014

Related U.S. Application Data

(60) Provisional application No. 61/799,441, filed on Mar. 15, 2013.

(51) Int. Cl.
*A61B 10/00* (2006.01)
*G01N 1/31* (2006.01)
*G01N 1/36* (2006.01)
*B01L 3/00* (2006.01)

(52) U.S. Cl.
CPC . *G01N 1/31* (2013.01); *B01L 3/508* (2013.01); *G01N 1/36* (2013.01); *B01L 2300/0609* (2013.01)

(58) Field of Classification Search
CPC .................................. G01N 1/31; G01N 1/36
See application file for complete search history.

(56) References Cited

U.S. PATENT DOCUMENTS

| 4,735,794 | A | 4/1988 | Parkinson |
| 5,401,625 | A | 3/1995 | Robinson |
| 5,447,841 | A | 9/1995 | Gray et al. |
| 5,601,650 | A | 2/1997 | Goldbecker et al. |
| 5,695,942 | A | 12/1997 | Farmilo et al. |
| 5,817,032 | A | 10/1998 | Williamson, IV et al. |
| 5,895,628 | A | 4/1999 | Heid et al. |
| 5,965,454 | A | 10/1999 | Farmilo et al. |

(Continued)

FOREIGN PATENT DOCUMENTS

| DE | 102007011329 A1 | 9/2008 |
| DE | 102008005265 A1 | 7/2009 |

(Continued)

*Primary Examiner* — Jyoti Nagpaul
(74) *Attorney, Agent, or Firm* — Sughrue Mion, PLLC

(57) ABSTRACT

An apparatus for holding a tissue sample having a retaining member with a first tissue engaging surface and at least one biasing element. The first tissue engaging surface is moveably attached to the retaining member. The apparatus also has a base comprising a second tissue engaging surface which is configured to engage the retaining member to form an interior area with the first and second tissue engaging surfaces facing each other. The apparatus also has a retracting member connected to the retaining member which is configured to retract the first tissue engaging surface and compress the biasing element to form a gap between the tissue sample and one of the first tissue engaging surface and the second tissue engaging surface.

27 Claims, 10 Drawing Sheets

(56) References Cited

U.S. PATENT DOCUMENTS

| | | |
|---|---|---|
| 5,968,436 A | 10/1999 | Takezaki |
| 6,042,874 A | 3/2000 | Visinoni et al. |
| 6,103,518 A | 8/2000 | Leighton |
| 6,207,408 B1 | 3/2001 | Essenfeld et al. |
| 6,311,945 B1 | 11/2001 | DAngelo |
| 6,329,645 B2 | 12/2001 | Giberson et al. |
| 6,372,512 B1 | 4/2002 | Kerschmann |
| 6,383,801 B1 | 5/2002 | Leighton |
| 6,444,170 B1 | 9/2002 | Heid et al. |
| 6,465,245 B1 | 10/2002 | Walton et al. |
| 6,468,783 B1 | 10/2002 | Leighton |
| 6,513,803 B2 | 2/2003 | Morales et al. |
| 6,521,186 B1 | 2/2003 | Izvoztchikov et al. |
| 6,586,713 B2 | 7/2003 | Essenfeld et al. |
| 6,596,479 B1 | 7/2003 | Gray et al. |
| 6,793,890 B2 | 9/2004 | Morales et al. |
| 6,797,928 B2 | 9/2004 | Giberson et al. |
| 6,803,018 B1 | 10/2004 | Stiller |
| 6,875,583 B2 | 4/2005 | Giberson et al. |
| 6,902,928 B2 | 6/2005 | Izvoztchikov et al. |
| 6,991,934 B2 | 1/2006 | Walton et al. |
| 7,005,110 B2 | 2/2006 | Taft et al. |
| 7,075,045 B2 | 7/2006 | Visinoni |
| 7,155,050 B1 | 12/2006 | Sloge et al. |
| 7,156,814 B1 | 1/2007 | Williamson, IV et al. |
| 7,179,424 B2 | 2/2007 | Williamson, IV et al. |
| 7,217,392 B2 | 5/2007 | Bogen et al. |
| 7,219,884 B2 | 5/2007 | Morales |
| 7,273,587 B1 | 9/2007 | Birkner et al. |
| 7,273,720 B1 | 9/2007 | Birkner et al. |
| 7,329,533 B2 | 2/2008 | Fredenburgh |
| 7,470,401 B2 | 12/2008 | Morales |
| 7,521,021 B2 | 4/2009 | McCormick |
| 7,526,987 B2 | 5/2009 | Morales |
| 7,544,953 B2 | 6/2009 | Goodman |
| 7,547,538 B2 | 6/2009 | Morales et al. |
| 7,553,672 B2 | 6/2009 | Bogen et al. |
| 7,575,556 B2 | 8/2009 | Speeg et al. |
| 7,576,307 B2 | 8/2009 | Yazdanfar et al. |
| 7,584,019 B2 | 9/2009 | Feingold et al. |
| 7,593,787 B2 | 9/2009 | Feingold et al. |
| 7,603,201 B2 | 10/2009 | Feingold et al. |
| 7,618,828 B2 | 11/2009 | Bleuel et al. |
| 7,657,070 B2 | 2/2010 | Lefebvre |
| 7,663,101 B2 | 2/2010 | Goodman |
| 7,666,620 B2 | 2/2010 | Wiederhold |
| 7,687,255 B2 | 3/2010 | Chu |
| 7,722,810 B2 | 5/2010 | Allen et al. |
| 7,767,434 B2 | 8/2010 | Chu |
| 7,776,274 B2 | 8/2010 | Williamson, IV et al. |
| 7,780,919 B2 | 8/2010 | McCormick |
| 7,850,912 B2 | 12/2010 | Favuzzi et al. |
| 7,881,517 B2 | 2/2011 | Sloge et al. |
| 7,888,132 B2 | 2/2011 | McCormick |
| 7,901,634 B2 | 3/2011 | Testa et al. |
| 7,914,462 B2 | 3/2011 | Hutchins et al. |
| 7,914,738 B2 | 3/2011 | Hutchins et al. |
| 2005/0084425 A1 | 4/2005 | Williamson, IV et al. |
| 2005/0112032 A1 | 5/2005 | McCormick |
| 2005/0142631 A1 | 6/2005 | Mosconi et al. |
| 2005/0147538 A1 | 7/2005 | Williamson, IV et al. |
| 2006/0147896 A1 | 7/2006 | Schnetz et al. |
| 2006/0177812 A1 | 8/2006 | Schnetz et al. |
| 2006/0228772 A1 | 10/2006 | Donndelinger |
| 2007/0072167 A1 | 3/2007 | Rochaix |
| 2007/0104618 A1 | 5/2007 | Williamson, IV et al. |
| 2007/0116612 A1 | 5/2007 | Williamson, IV |
| 2007/0141711 A1 | 6/2007 | Stephens et al. |
| 2007/0161609 A1 | 7/2007 | Buck et al. |
| 2007/0166834 A1 | 7/2007 | Williamson, IV et al. |
| 2007/0218542 A1 | 9/2007 | Li et al. |
| 2008/0026366 A1 | 1/2008 | Harkins |
| 2008/0138854 A1 | 6/2008 | Williamson |
| 2008/0193014 A1 | 8/2008 | Ecker et al. |
| 2008/0206807 A1 | 8/2008 | Duymelinck et al. |
| 2008/0220468 A1 | 9/2008 | Windeyer et al. |
| 2008/0227144 A1 | 9/2008 | Nightingale |
| 2008/0254504 A1 | 10/2008 | Vom et al. |
| 2008/0268496 A1 | 10/2008 | Mosconi et al. |
| 2008/0274496 A1 | 11/2008 | Duymelinck et al. |
| 2009/0098522 A1 | 4/2009 | Marcovitz |
| 2009/0145920 A1 | 6/2009 | Kerrod et al. |
| 2009/0165940 A1 | 7/2009 | Baur et al. |
| 2009/0170152 A1 | 7/2009 | Reeser et al. |
| 2009/0191544 A1 | 7/2009 | DeLa Torre Bueno |
| 2009/0203066 A1 | 8/2009 | Perrut et al. |
| 2009/0208105 A1 | 8/2009 | Bystrov et al. |
| 2009/0222746 A1 | 9/2009 | Chirica et al. |
| 2009/0253199 A1 | 10/2009 | McCormick |
| 2010/0017030 A1 | 1/2010 | Feingold et al. |
| 2010/0055663 A1 | 3/2010 | Konrad et al. |
| 2010/0061632 A1 | 3/2010 | Young et al. |
| 2010/0075410 A1 | 3/2010 | Desai et al. |
| 2010/0092064 A1 | 4/2010 | Li |
| 2010/0093023 A1 | 4/2010 | Gustafsson et al. |
| 2010/0099140 A1 | 4/2010 | Donndelinger |
| 2010/0112624 A1 | 5/2010 | Metzner et al. |
| 2010/0112625 A1 | 5/2010 | Erben et al. |
| 2010/0144002 A1 | 6/2010 | Donndelinger |
| 2010/0167334 A1 | 7/2010 | Williamson, IV |
| 2010/0167338 A1 | 7/2010 | Amano et al. |
| 2010/0182877 A1 | 7/2010 | Chu |
| 2010/0184127 A1 | 7/2010 | Williamson, IV et al. |
| 2010/0208955 A1 | 8/2010 | Mehes et al. |
| 2010/0223935 A1 | 9/2010 | Donndelinger |
| 2010/0248301 A1 | 9/2010 | Ulbrich et al. |
| 2010/0278627 A1 | 11/2010 | Williamson, IV et al. |
| 2010/0279341 A1 | 11/2010 | Steiner et al. |
| 2010/0323395 A1 | 12/2010 | Ulbrich et al. |
| 2010/0330660 A1 | 12/2010 | Hutchins et al. |
| 2011/0008884 A1 | 1/2011 | Morales |
| 2011/0034341 A1 | 2/2011 | Mehes et al. |
| 2011/0045565 A1 | 2/2011 | Sanders et al. |
| 2011/0054679 A1 | 3/2011 | Lefebvre et al. |
| 2011/0060766 A1 | 3/2011 | Ehlke et al. |
| 2011/0076753 A1 | 3/2011 | Goerner et al. |

FOREIGN PATENT DOCUMENTS

| | | |
|---|---|---|
| DE | 102009010667 A1 | 9/2010 |
| EP | 1545775 | 9/1985 |
| EP | 0807807 A1 | 11/1997 |
| EP | 1508026 | 2/2005 |
| EP | 1682272 | 7/2006 |
| EP | 1782737 A1 | 5/2007 |
| EP | 1975595 A1 | 10/2008 |
| EP | 1985383 A1 | 10/2008 |
| EP | 2002894 A1 | 12/2008 |
| EP | 2091440 | 8/2009 |
| WO | 2004/028693 A1 | 4/2004 |
| WO | 2005/037182 A2 | 4/2005 |
| WO | 2008/073387 A1 | 6/2008 |
| WO | 2010/030358 A1 | 3/2010 |
| WO | 2010/085626 A1 | 7/2010 |
| WO | 2010/112316 A1 | 10/2010 |
| WO | 2011041495 A1 | 4/2011 |

TISSUE CASSETTE WITH RETRACTABLE MEMBER

BACKGROUND OF THE INVENTION

The present invention relates generally to a tissue cassette for retaining a tissue sample having a retractable member for retracting the surface which retains the tissue sample.

After a tissue sample is collected, the tissue sample is analyzed at a lab (e.g. a pathology lab, biomedical lab, etc.) that is set up to perform the appropriate tests (such as histological analysis). In order to properly process the tissue sample a series of steps may be performed including:
1. Grossing of the sample by cutting the sample to the proper size for analysis.
2. Fixing of the sample to immobilize molecular components and/or prevent degradation.
3. Embedding the sample in an embedding material, such as paraffin wax
4. Sectioning the embedded sample by using, for example, a microtome.

In conventional methods, the grossing step involves a lab technician cutting the tissue to the appropriate size for analysis and then placing the tissue in a tissue cassette. During the fixation stage, the cassettes are generally exposed to a fixing agent or chemical (e.g., a solution of formaldehyde in water such as formalin) shortly after sample collection. For example, U.S. Pat. No. 7,156,814 discloses a cassette which can withstand tissue preparation procedures.

After the tissue sample has been processed, the medical professional, in conventional methods, removes the tissue sample from the individual cassette to perform the embedding step. Specifically, the medical professional carefully orients the sample, based on the diagnostic view required, into a base mold containing an embedding material such as paraffin wax. Once the tissue is oriented properly in the base mold, the molten material is cooled to fully embed the tissue sample and hold it in the proper orientation. The paraffin is used to hold the sample in position while also providing a uniform consistency to further facilitate sectioning. While the term paraffin is used, this term is not limiting and describes an example of an embedding medium. Further, the term sample is not limiting and can refer to one or more tissue samples.

After the sample is embedding in paraffin, the embedded paraffin is sliced into a plurality of thin sections (e.g., 2 to 25µ thick sections), often using a microtome, for further processing and inspection. Such sectioning of the sample often helps a medical professional properly assess the sample under a microscope (e.g. diagnose relationships between cells and other constituents of the sample, or perform other assessments).

The current process requires human intervention at both the grossing and embedding steps. Such manual handling of the sample can increase the likelihood of mis-identifying the sample, cross contaminating the samples, or losing part of the sample or the entire sample. Additionally, the numerous steps of manual manipulation can often increase the time that it takes to provide a proper assessment for each sample, once the sample is collected.

SUMMARY OF THE INVENTION

In view of the foregoing, aspects of the present invention are provided to allow for reduced manual manipulation of a tissue sample after it is oriented and placed in a tissue cassette and also to maintain the identity of the tissue sample.

Accordingly, in an illustrative non-limiting embodiment, a tissue cassette for holding a tissue sample with a retractable surface is provided such that the tissue sample may be oriented and placed into the tissue cassette, and embedded with paraffin in the tissue cassette to maintain orientation of the tissue sample. The tissue cassette has a retaining member having an first tissue engaging surface and a biasing element. The first tissue engaging surface is moveably attached to the retaining member by the biasing element. The tissue cassette also has a base comprising a second tissue engaging surface. The second tissue engaging surface of the base is configured to engage the retaining member such that when the first and second tissue engaging surfaces face each other an interior area is formed. The biasing element is configured to urge the first tissue engaging surface toward the second tissue engaging surface to retain the tissue sample therebetween in the interior area. Further a retracting member is disposed on the retaining member and is configured to retract the first tissue engaging surface and compress the biasing element to form a gap between the tissue sample and one of the first tissue engaging surface and the second tissue engaging surface such that paraffin can fill the gap.

DETAILED DESCRIPTION OF THE INVENTION

The following description, of illustrative, non-limiting embodiments of the invention, discloses specific configuration and components. However, the embodiments are merely examples of the present invention, and thus, the specific features described below are merely used to more easily describe such embodiments and to provide an overall understanding of the present invention. Accordingly, one skilled in the art will readily recognize that the present invention is not limited to the specific embodiments described below. Furthermore, the descriptions of various configurations and component of the present invention that are known to one skilled in the art are omitted for the sake of clarity and brevity.

Figure 1A:
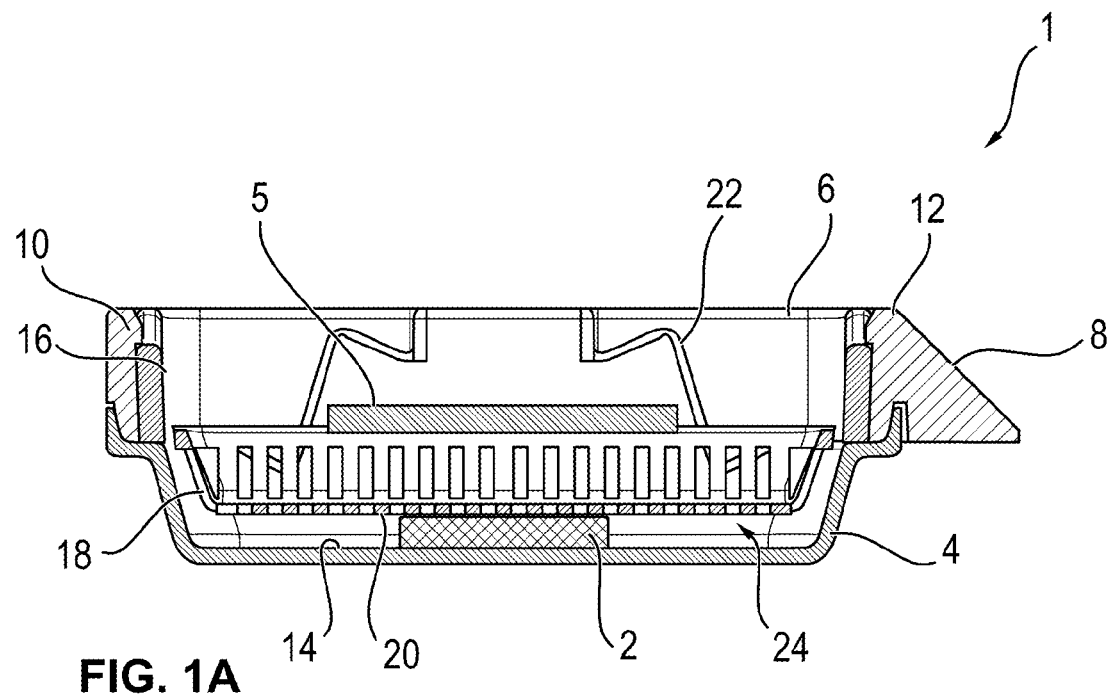
FIG. 1A is an interior side view of an assembled tissue cassette according to a first embodiment with the retaining element in a non-retracted state.

FIG. 1A shows an apparatus for holding a tissue sample according to an illustrative, non-limiting embodiment of the present invention. As shown, a tissue cassette 1 retains a tissue sample 2 in the proper orientation to allow for the automation of the processing and a reduction in human error. A similar tissue cassette is disclosed in U.S. Patent Application No. 61/798,728, title "Tissue Cassette with Biasing Element" which is incorporated herein by reference.

The tissue cassette 1, according to one embodiment of the invention, has a base 4 and a retractable retaining member 6 which cooperate to retain the tissue sample 2, as well as a retracting member 5 for retracting the retaining member 6, as discussed below. In addition, a frame 8 may optionally be provided to surround the outer perimeter of the retaining member 6 and attach to the retaining member with locking member 10. In this way, the retaining member 6 fits into the inside perimeter of the base 4, and the base 4, retaining member 6, and frame 8 are sealed by sealing member 12. The sealing member forms a liquid seal between the retaining member 6 and the base 4 to prevent liquid from leaking between the retaining member 6 and the base 4.

FIG. 1A further shows a base 4 with a bottom surface which corresponds to a second tissue engaging surface 14 and is configured to receive a tissue sample 2 in its desired orientation. Positioned over the base 4, the retaining member 6 is formed with a rim portion 16 and a retaining element 18 having a bottom surface corresponding to a first tissue engaging surface 20. Generally, when the base 4 and the retaining member 6 are engaged as shown in FIG. 1A, an interior area 24 is defined between the base 4 and the retaining member 6 where the first tissue engaging surface 20 and the second tissue engaging surface 14 are facing each other.

In a non-limiting embodiment, the retaining element 18 is attached to the rim portion 16 by a biasing element 22. Upon engagement of the retaining member 6 to the base 4, the biasing element 22 urges the first tissue engaging surface 20 of the retaining element 18 downwardly away from the rim portion 16 and towards the second tissue engaging surface 14 of the base 4 to firmly hold the tissue sample 2 in the chosen orientation between the first and second tissue engaging surfaces 14, 20 such that it can later be embedded with paraffin or the like. In addition, a retracting member 5 is attached to the retaining member 6 to compress the biasing element 22 and retract the retaining element 18 upwardly away from the tissue sample 2.

Figure 1B:
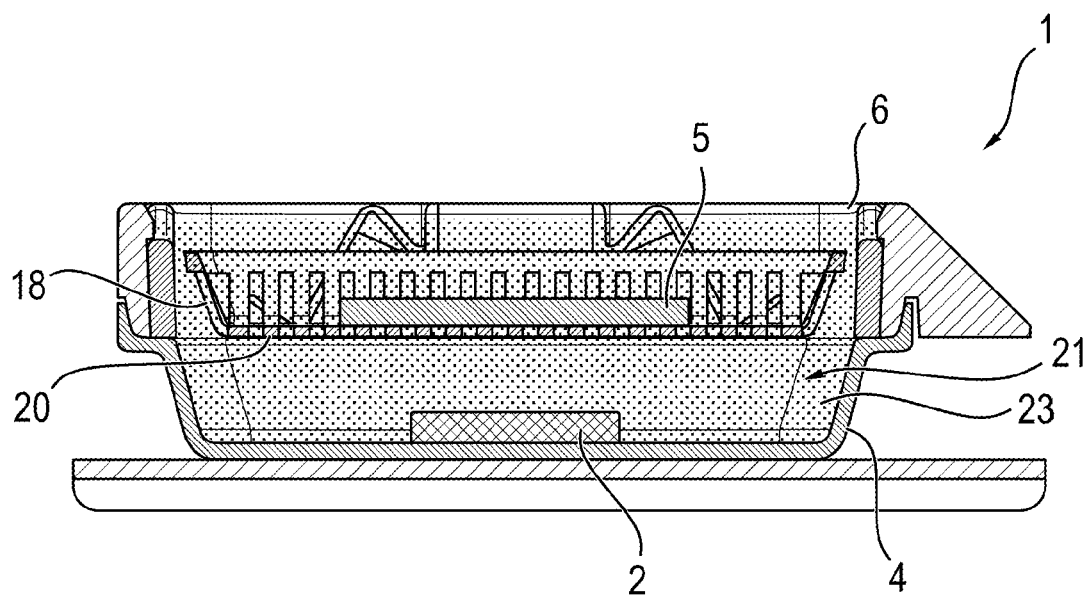
FIG. 1B an interior side view of the tissue cassette of FIG. 1A with the retaining element in a retracted state.

As shown in FIG. 1B, paraffin 21 is added to the tissue cassette 1 to embed the tissue sample 2. After the paraffin 21 has been added to the tissue cassette 1, the tissue cassette 1 is held against a chilling surface such that the paraffin at the bottom of the tissue cassette 1 starts to cool. When the paraffin starts to cool, a first, thin layer of solidified paraffin 23 adheres the tissue sample 2 to the base to partially secure the tissue sample 2 to the base 4. As discussed in greater detail below, while the paraffin 21 is still molten, the retracting member 5 connected to the retaining member 6 pulls the first tissue engaging surface 20 of the retaining element 18 away from the tissue sample 2 and through the semi-molten paraffin such that the paraffin can contact the surface of the tissue sample 2. According to this embodiment the retracting member 5 is a ferromagnetic member which responds when a magnetic field is introduced to compress the biasing element 22 and retract the first tissue engaging surface 20. As discussed below with reference to FIGS. 4A-4B, the retracting member 5 allows the retaining element 18 to be separated from the embedded tissue sample for sectioning and analysis of the embedded tissue sample. As such, the first tissue engaging surface 20 may be held in a position away from the tissue sample 2 until the remaining paraffin has solidified. Once the paraffin 21 has solidified, the base 4 may be removed from the tissue cassette 1 to expose the embedded tissue sample and allow for sectioning of the embedded tissue sample (not shown).

Figure 2:
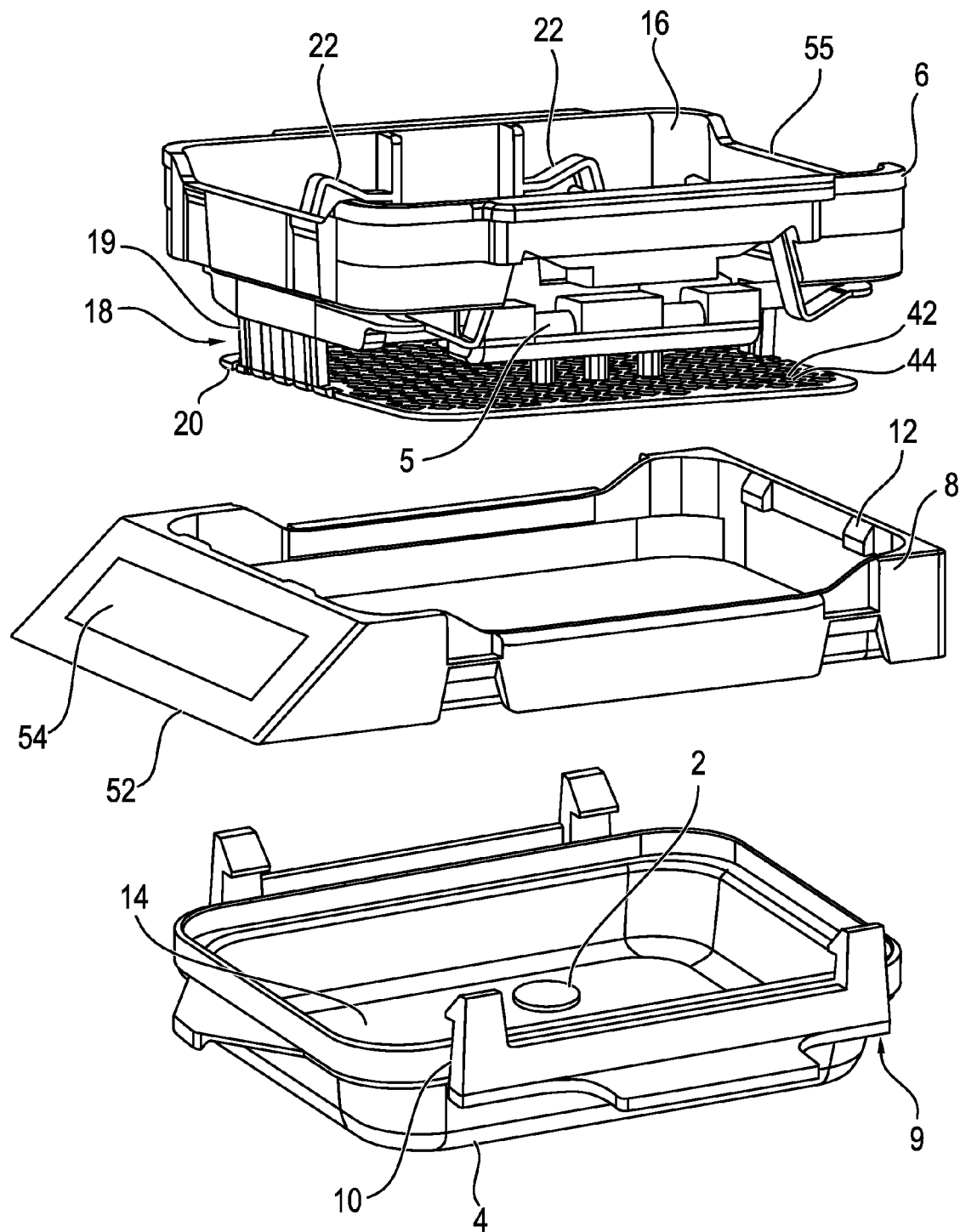
FIG. 2 is an exploded view of the tissue cassette according to the first embodiment of the present invention in a non-assembled state.

The individual components of the tissue cassette, including the retracting member, will now be described in more detail. FIG. 2 shows an exploded view of the tissue cassette 1 according to a non-limiting embodiment. In this exemplary embodiment, the retaining member 6 has a rim 16, a biasing member 22 which connects the rim 16 to the retaining element 18, and a first tissue engaging surface 20 on the retaining element 18. Further, as shown in FIG. 2, a connector 19 may be provided to connect the first tissue engaging surface 20 to the biasing element 22.

The rim 16 is provided with four walls and a substantially rectangular shape. On the inside of the rim 16 one end of the biasing member 22 is attached. The other end of the biasing member 22 attaches to the retaining element 18 at either a connector 19 or the first tissue engaging surface 20.

As shown in FIG. 2, the first tissue engaging surface 20 is provided with a substantially planar mesh portion 42. In this embodiment the mesh portion 42 is rectangular in shape, but the shape is not limiting and the mesh portion 42 can be a variety of shapes. The mesh portion 42 of the first tissue engaging surface 20 has a plurality of perforations 44 or cut-outs. When the mesh portion 42 is urged against the tissue sample 2 it holds the tissue sample 2 in place and allows reagents, or the like, to flow to the tissue sample 2 through the perforations 44 in the mesh portion 42. The perforations 44 are sized to allow the flow of fluid to the tissue sample 2 on the one hand, but to prevent the escape of the tissue sample 2 on the other hand. Thus, the perforations 44 in the mesh portion 42 may be sized according to the size of the tissue sample 2. Further, the first tissue engaging surface 20, may alternatively be solid and have no holes on the surface while still allowing the agent to flow underneath the first tissue engaging surface 20 from the periphery.

Figure 3:
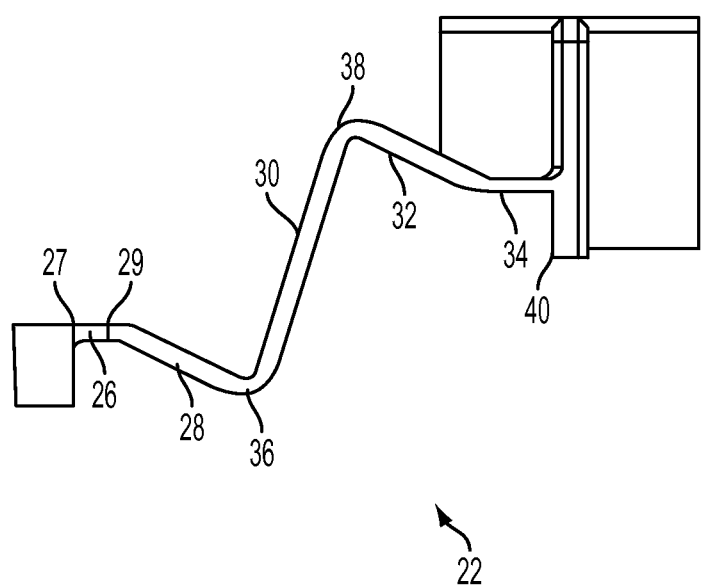
FIG. 3 shows a cut-out section of the biasing element on the tissue cassette of the above embodiment.

As shown in FIG. 3, each biasing element 22 may in some embodiments is substantially hinged having an S or Z shape and attached at one end to the retaining element 18 and attach at the other end to the inner surface of the rim portion 16. In the illustrated embodiment in FIG. 2, the tissue cassette 1 has four biasing elements 22, where two biasing elements are shown in the Figure on one wall and the other two are on the opposite wall. The biasing element 22 urges the retaining element 18 towards the base 4 to fix the tissue sample 2 between the first and second tissue engaging surfaces 14, 20. Thus, the biasing element 22 can take on any shape that performs this function. For example, a torsion bar or a biasing element having another shape could also be used as discussed in more detail below.

More specifically, an example of a biasing element 22 is shown in FIG. 3. Each biasing element 22 has a first member 26 with a first end 27 and a second end 29. The first end 27 is connected to the retaining element 18. Extending downward at an angle from the hinge or second end 29 of the first member 26 is a first angled member 28. A second angled member 30 is connected to the first angled member 28 by a first curved hinged point 36. The second angled member 30 extends upwardly from the first angled member 28 at an angle; and in a non-limiting embodiment, the second angled member 30 and the first angled member 28 form an angle less than 90°. Extending downwardly from the second angled member 30 is a third angled member 32. The second angled member 30 and the third angled member 32 are connected by a second curved hinge point 38. In a non-limiting embodiment, the third angled member 32 and the second angled member 30 form an angle less than 90°. Further, in a non-limiting embodiment, the third angled member 32 and the first angled member 28 form an angle less than 90°. A second member 34 connects to the third angled member 32 at a hinge point and extends substantially parallel to the retaining element 18. The second member 34 attaches to the rim portion 16 of the retaining member 6 in a non-limiting embodiment.

The base 4 will now be described with reference to FIG. 2. As discussed above, the tissue cassette 1 has a base 4 which supports the tissue sample 2 and holds the paraffin for embedding. The base 4 has a generally rectangular shape with four side walls and a depressed bottom planar surface, referred to as the second tissue engaging surface 14. The base 4 is not limited to this shape and a different shape could be used without changing the scope of the invention. The base 4 is preferably solid so that it can hold the paraffin for embedding. The walls of the base 4 are preferably tapered inward to improve the ease at which the base can be removed from the paraffin after the embedding process.

As noted above, in some embodiments a frame 8 is placed around the outside perimeter of the retaining member 6 and functions to secure the retaining member 6 to the base 4. The frame 8 may also be used as a means for identifying the tissue sample. As shown in FIG. 2, the frame 8 has a substantially rectangular shape with one end have an angled projection with an angled face 52. As shown in FIG. 2, a label 54 may be placed on the angled face 52 to identify the tissue sample 2. The labels 54 are described in more detail below. In this embodiment, the angle of the planar face is about 45 degrees, but the invention is not limited in this respect.

In a non-limiting embodiment, the frame 8 and the retaining member 6 are not easily removed so that once the tissue cassette 1 is used, the label 54 on the frame 8 will remain matched with the tissue sample 2 contained in the tissue cassette 1. In certain embodiments, frame 8 has a locking projections 12 which projects from the inside the perimeter of the frame 8, shown in FIG. 1. The locking projections 12 attach with an engaging portions 55 on the outer perimeter of the rim portion 16 on the retaining member 6 to secure the frame 8 to the retaining member 6. Once the frame 8 is connected to the base 4 using this locking arrangement, it is difficult to separate them.

The base 4 includes a latching member 9 which acts as a clip or lock to hold the base 4 to the frame 8. Alternatively, if a frame 8 is not used, the latching member 9 can lock the base 4 to the retaining member 6.

As shown in FIG. 2, the latching member 9 is connected to a releasing member 60. The latching member 9 is flexibly attached to the base 4. When the latching member 9 is engaged, the latching member 9 attaches to the clip surfaces 56 on the outer perimeter of the frame 8. The latching member 9 locks the base 4 to the frame 8 which is attached to the retaining member 6. In this way, a sealing member 10 connects the latching member 9 to the base 4 to form a seal between the surfaces on the perimeter of the base 4 and the frame 8 to sufficiently prevent paraffin from leaking during embedding. In a non-limiting embodiment a gasket may be used as the sealing member 10 to help seal the base 4 and the frame 8. The latching member 9 is disengaged by pressing downward on the releasing member 60. When the releasing member 60 is pressed, the latching member 9 moves away from the base 4 and disengages from the clip surfaces 56. In the embodiment described above, the sealing member 10 extends from the base 4, but the sealing member 10 may also extend from the retaining member 6 or the frame 8.

An important aspect of tissue sample analysis is properly keeping track of tissue samples. In some embodiments, the tissue cassette 1 includes a label 54 or ID tag as shown in FIG. 2. The label can 54 be located anywhere on the tissue cassette 1, but is preferably located on the frame 8. In some embodiments, more than one tag may be present. When more than one tag is present, the tags can be physically separated or located together.

The label 54 may be a computer or human readable tag including, but not limited to, labels having an incorporated RFID, labels having an incorporated one-dimensional barcode (1-D barcode), labels having an incorporated two-dimensional barcode (2-D barcode), and labels having an incorporated three-dimensional barcode (3-D barcode). However, the computer readable label is not limited to RFID, 1-D barcode, 2-D barcode, or 3-D barcode labels and may include any type of label readable by a computer as would be apparent to a person of ordinary skill in the art.

In some embodiments, a label 54 is present that may be sensitive to changes to the sample or itself. For example, a label 54 may be present that changes physical (i.e. color) or chemical (i.e. redox, conjugation, etc.) properties during fixation of the sample. Similarly, a label 54 may be present that is sensitive to the processing steps which precede embedding (i.e. dehydration). Alternatively, a label 54 may be present that is sensitive to the embedding step (i.e. infiltration of paraffin). The label 54 may have a property that changes incrementally or switches when the step is complete. In this way, the technician, or an automated system, will be able to determine when the sample has finished one step before another is started.

The tissue cassette 1 can be made from various materials and the same or different materials can be used for the retaining member 6, including the retaining element 18, the first tissue engaging surface 20, the mesh portion 42, and the base 4. Examples of materials used include: an acetal copolymer, Teflon, polypropylene, and stainless steel. In a non-limiting embodiment, the acetal copolymer is DELRIN 900. In a non-limiting embodiment, the base 4 is made out of a polypropylene material so that the base 4 does not attach to the paraffin after the tissue sample 2 is embedded.

In a non-limiting embodiment, the tissue cassette, including the base, the retaining member, and/or the frame, may be produced from a material lacking any dye or coloring. The lack of color may allow the technician to view the tissue sample in the tissue cassette and ensure that the tissue sample has remained in its desired orientation after embedding. In these embodiments, the tissue cassette, including the base, the retaining member, and/or the frame may be at least at least opaque or clear.

Some examples of retracting member 5 will now be described in additional detail. As previously stated and shown with respect to FIGS. 1A and 1B, the retracting member 5 is disposed on the retaining member 6 for compressing the biasing element 22 and retracting the retaining element 18 from the tissue sample 2. The retracting member 5 retracts the first tissue engaging surface 20 of the retaining element 18 from the tissue sample 2 and can take on any form or shape that serves this function.

Figure 4A:
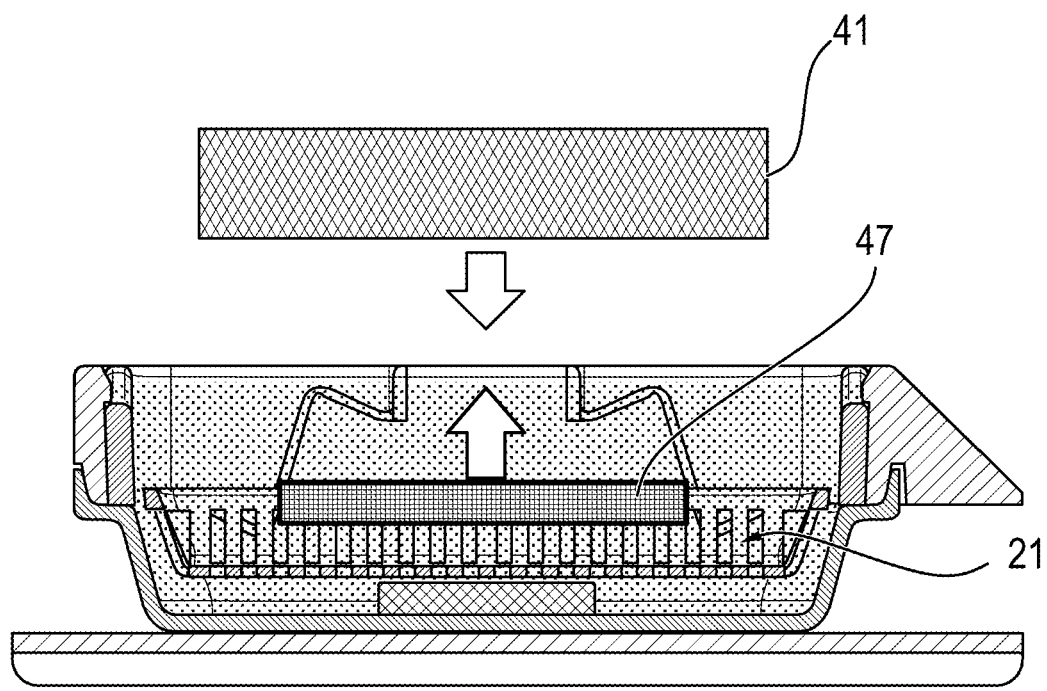
FIGS. 4A and 4B illustrate the tissue cassette according to one embodiment where the retracting member is a magnetic member
Figure 4B:
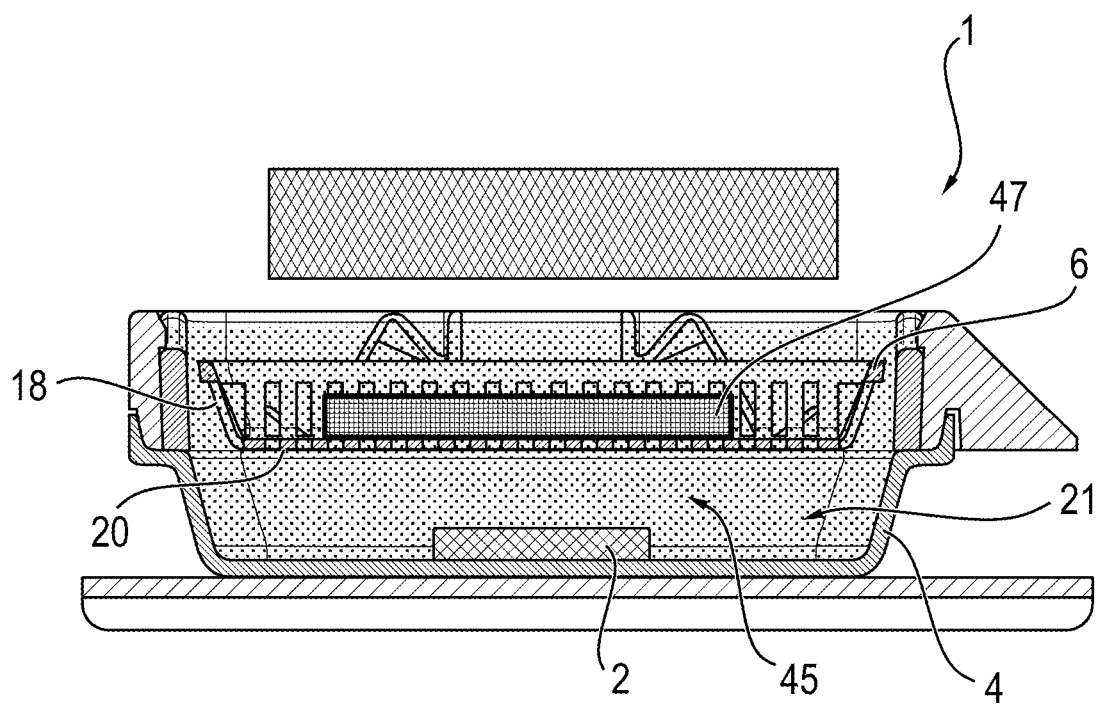

As shown in FIGS. 4A and 4B, the retracting member 5 may be provided as a ferromagnetic member 47. The ferromagnetic member 47 is connected to the retaining element 18 and in certain non-limiting embodiments is insert molded to the first tissue engaging surface 20. Alternatively, the ferromagnetic member 47 may be divided into smaller components and incorporated in the mesh structure 42 of the first tissue engaging surface 20.

FIG. 4A illustrates that after the tissue cassette 1 has been filled with paraffin 21 and placed on a chilling surface, a magnetic field is introduced by a magnetic instrument 41. By way of example, the magnetic instrument 41 is introduced approximately 30 seconds after the paraffin has been placed in the tissue cassette 1. The introduction time is paraffin grade dependent and not limiting to this invention. The magnetic field can be introduced either by permanent magnets being moved closer to the tissue cassette, electromagnets being powered up, some combination of the both, or any other example obvious to one of ordinary skill in the art.

The magnetic field introduced by the magnetic instrument 41 attracts the ferromagnetic member 47 and moves the first tissue engaging surface upwardly to compress the biasing element 22. The first tissue engaging surface 20 will stop retracting once it contacts a dead stop 40 (as shown in FIG. 3). The dead stop 40 may be provided on the biasing element 22, the frame 8, or the retaining member 6. Thus, a gap 45 will be formed between the tissue sample 2 and the first tissue engaging surface 20 so that the paraffin completely covers the upper surface of the tissue sample, as shown in FIG. 4B. Further, in certain non-limiting embodiments, the base will have flow channels such that the paraffin may cover the bottom surface of the tissue sample. The magnetic force is maintained until the paraffin solidifies enough such that the mesh will not fall back through the paraffin once the magnetic force stops.

Figure 5A:
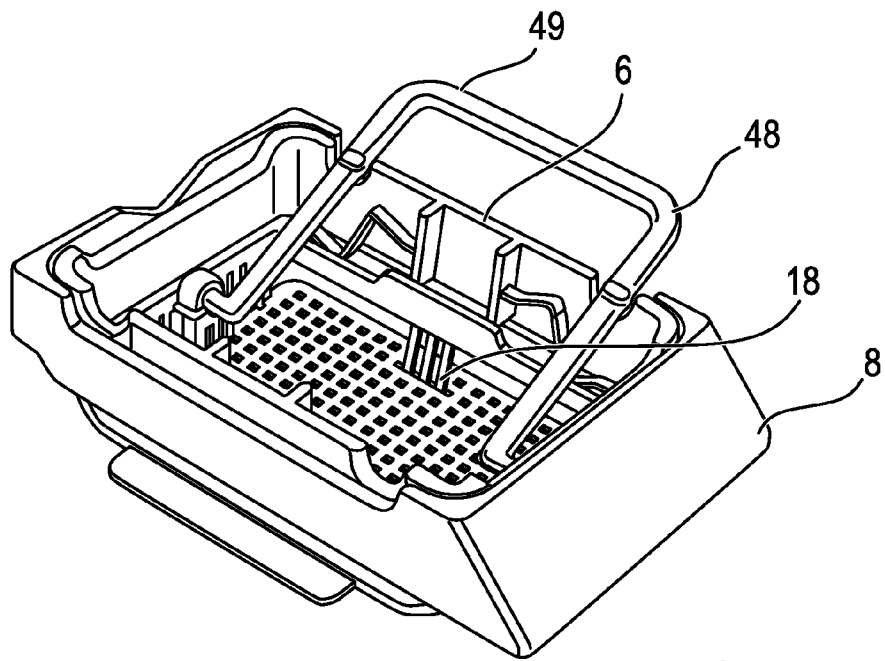
FIGS. 5A-5C illustrate the tissue cassette according to several embodiments where the retracting member is mechanical member.
Figure 5B:
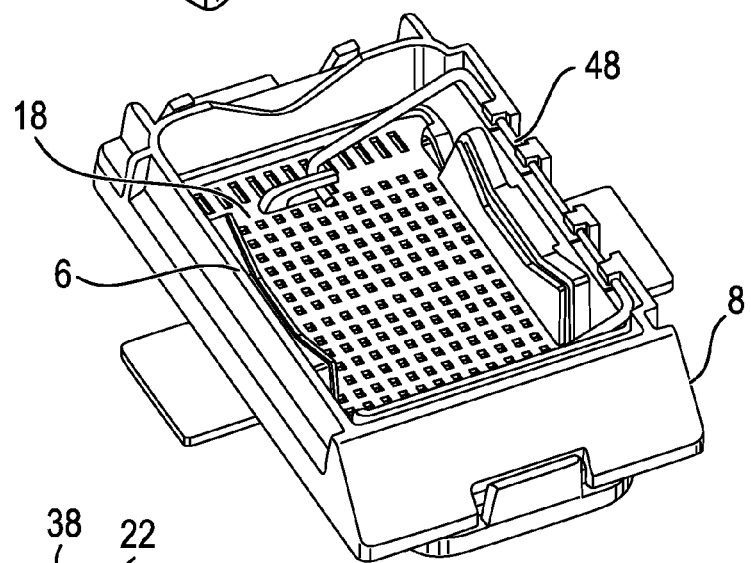
Figure 5C:
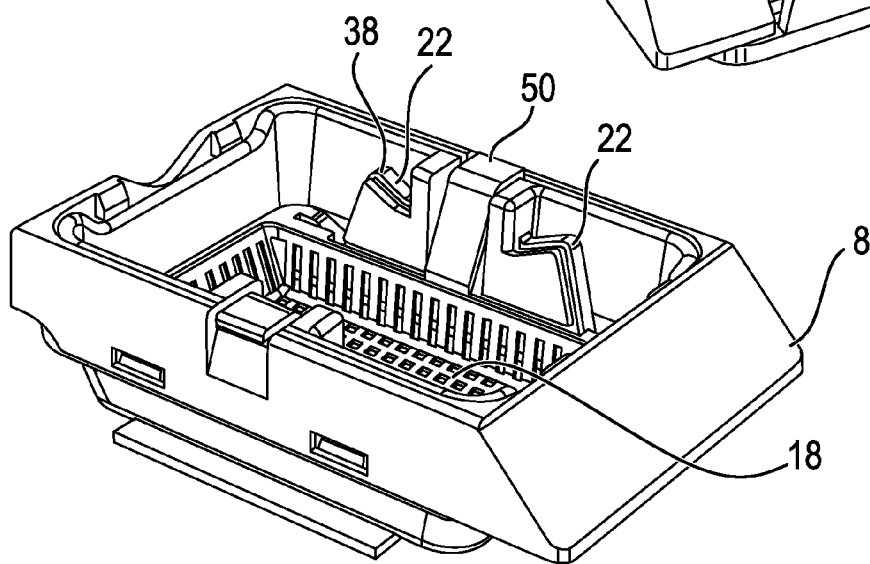
Figure 6:
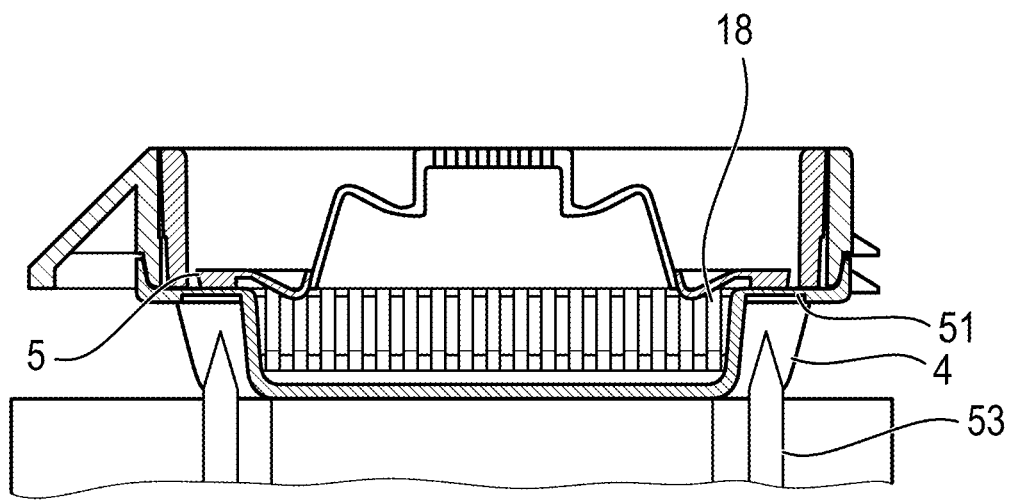
FIG. 6 is an interior side view of a tissue cassette according to another embodiment in an assembled state.
Figure 7:
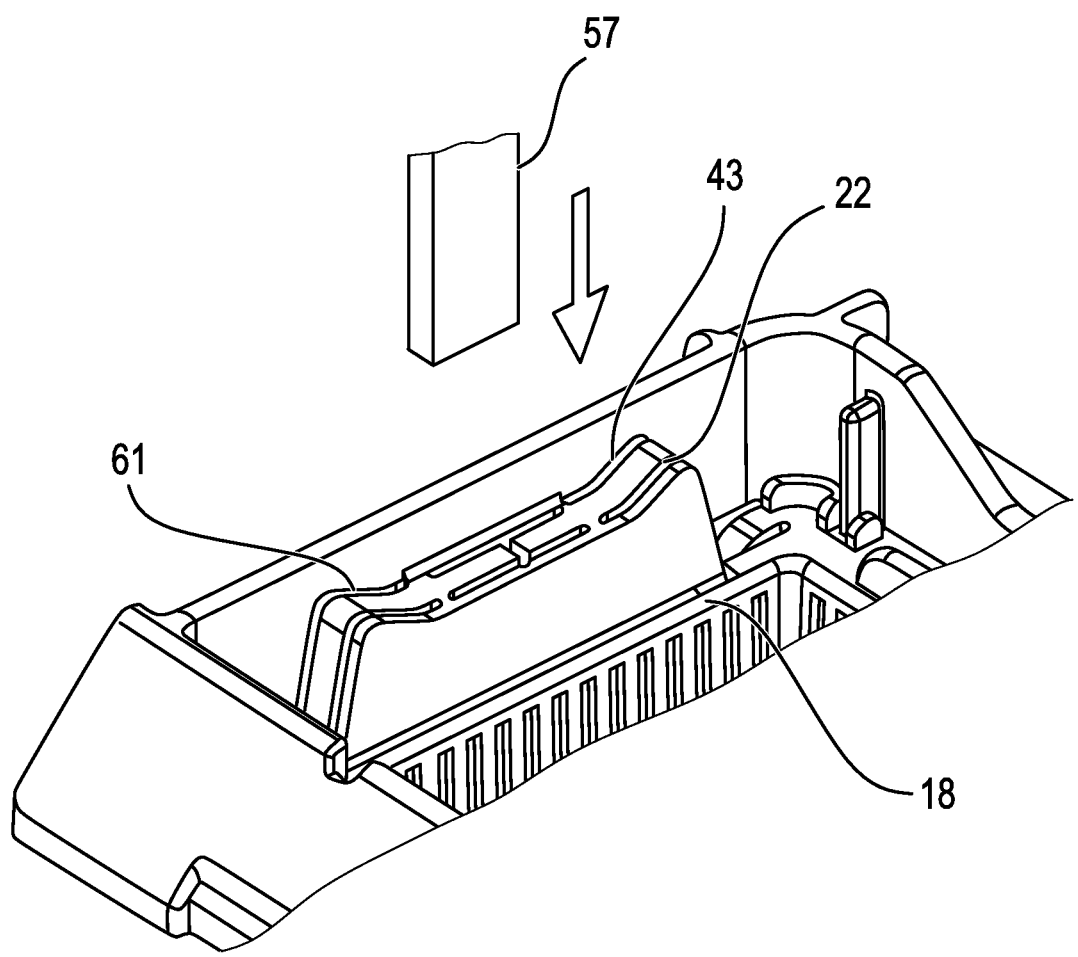
FIG. 7 is a cut-out view of a tissue cassette according to another embodiment in an assembled state.

FIGS. 5-7 illustrate alternative embodiments where the retracting member 5 comprises a mechanical member, such as a lever, a tab, or contact point. All other aspects of these embodiments have the same features of the embodiments described above.

For example, as shown in FIG. 5A, a lever 48 is provided on the retaining member 6 and is attached to the retaining element 18. A portion of the lever 48 hangs over the edge of the frame 8 such that a mechanism driven from above can push down on the overhanging portion 49 of the lever 48 and cause the retaining element 18 to move up, away from the tissue sample 2 (not shown).

FIG. 5B shows an alternate embodiment where the lever 48 provided does not hang over the side of the frame 8. In this example the lever 48 can be pulled upward by an external tool 57 (not shown) to cause the retaining element 18 to move away from the tissue sample 2. FIG. 5B illustrates the lever in a retained/non-retracted state.

In another exemplary embodiment, shown in FIG. 5C, tabs 50 are provided on the biasing element 22. The tabs 50 are connected to the retaining member 6 or biasing element 22 and are provided substantially in the center of the two biasing elements 22 to hang over the outer surface of the frame 8. The tabs 50 may be flush with the side of frame 8 and the frame 8 may be indented as shown in FIG. 5C to allow for the tabs 50 to be pushed or pulled by a tool 57 which contacts the exterior portion of the tabs. The tabs 50 may be pulled or pushed upward such that the retaining element 18 moves away from the tissue sample and the biasing element 22 is compressed. While FIG. 5C shows one tab 50 on each side of the tissue cassette 1, more than one tab may be provided and may be located anywhere on the retaining member 6 or biasing element 22. For example, two tabs 50 may extend from each second curved hinge point 38 of the biasing element 18. Alternatively, a tool 57 could be provided to contact underneath the second curved hinge point 38 of each biasing member and pull up on the second curved hinge point 38 to contract the biasing element 22.

FIG. 6 shows another exemplary embodiment of the retracting member. In this instance the retracting member 5 is disposed on the edge of the retaining element 18. Further, the base 4 has locally weak areas 51 such that pins 53 pierce the locally weak areas 51 in the base 4. The pins 53 push through the base 4 and contact the retracting member 5 on the retaining element 18 to push through and lift up the retaining element 18.

FIG. 7 illustrates another exemplary embodiment of the retracting member such that the biasing element 22 is provided with a plurality of torsion tabs 61. In this example, the torsion tabs 61 extend along an upper surface of the biasing element 22 to connect the two biasing elements. As such, when a tool 57 presses down on the center of the torsion tab 61, the torsion tabs 61, being connected to each biasing element 22, deflect upwardly on an outer portion of the biasing element. This pressure to the torsion tabs 61 compresses the biasing elements 22 such that the retaining element 18 is pulled up and away from the tissue sample 2. Examples of materials used for the torsion tab include: an acetal copolymer, Teflon, polypropylene, and stainless steel. In a non-limiting embodiment, the acetal copolymer is DELRIN 900. In some embodiments, the torsion tab may be molded integral with the tissue cassette 1.

Figure 8A:
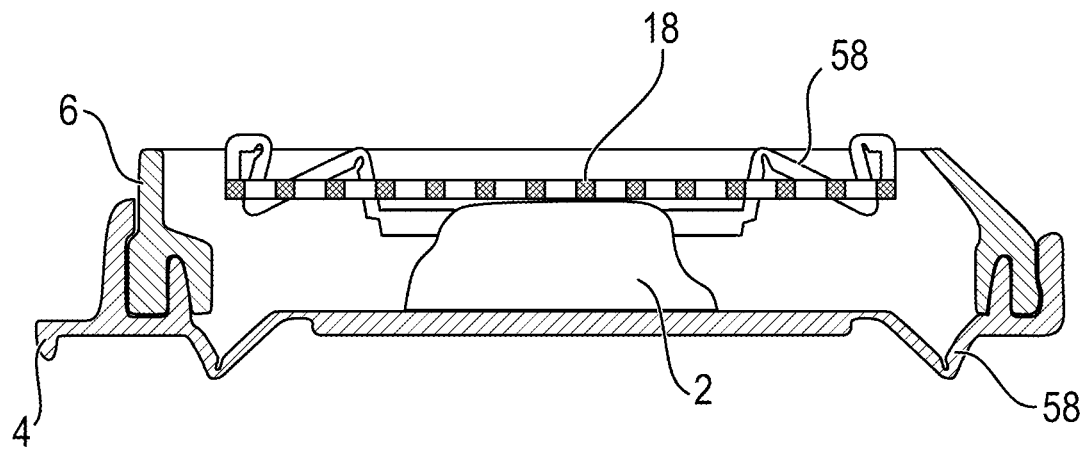
FIGS. 8A and 8B are interior side views of a tissue cassette according to another embodiment in an assembled state.
Figure 8B:
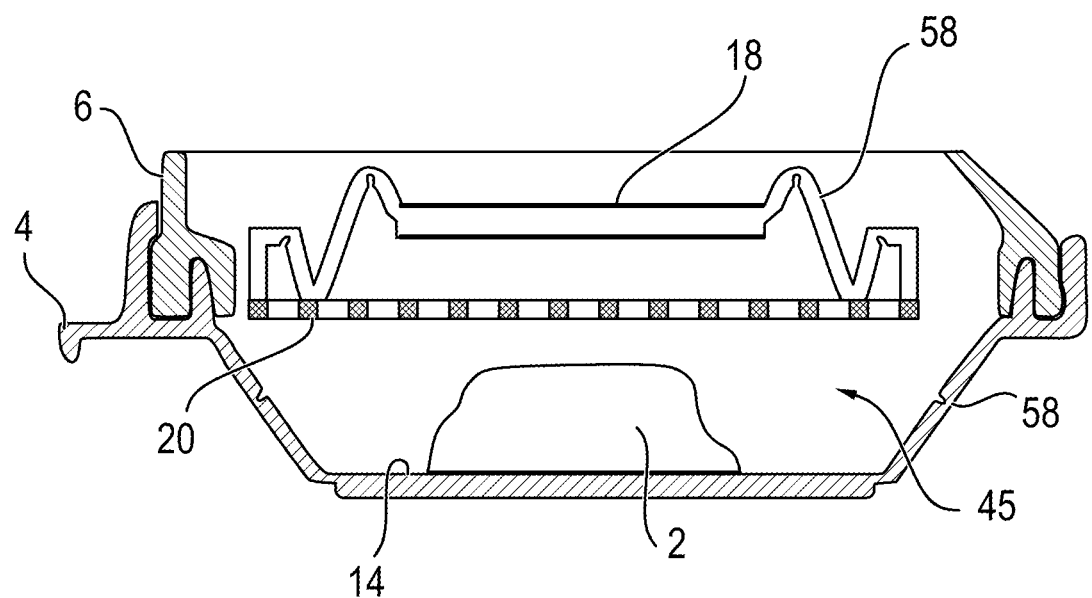

FIGS. 8A and 8B show another embodiment of the present invention in which the retaining element 18 is flexibly attached to the base 4 and the retaining member 6. In this example biasing members 58 may be attached to the retaining member 6, the base 4, or both the retaining member 6 and the base 4. Thus, in this instance, paraffin 21 (not shown) may be added to the tissue cassette 1 to secure the tissue sample 2 to the base 4. FIG. 8A shows an unreleased condition. Then the biasing members 58 on the base 4 may be released to move the base 4 away from the tissue sample 2 as shown in FIG. 8B in the released condition. Thus, when the base 4 is released, the tissue sample 2 is provided on the base and a gap 45 is provided between the first tissue engaging surface 20 and the second tissue engaging surface 14. Accordingly, paraffin may fill the gap 45 and embed the tissue sample 2. In this embodiment, the tissue sample container 1 is stable when either the biasing member 58 attached to the retaining member 6 or biasing member 58 attached to the base 4 is applying a biasing force, or when both are applying or not a biasing force.

For example, in this non-limiting embodiment, the biasing member 58 on the base 4 may be used only to enable the releasing of the force that is applied by the biasing member 58 on retaining member 6. As an example, in this embodiment, the tissue cassette 1 provides a two position floor. The first position is when the biasing member 58 on the base 4 compresses the second tissue engaging surface 14 upwardly such that the tissue engaging surface is compressed up towards the retaining member 6 to compress the tissue sample 2. The second position is when the force of the biasing member 58 on the base is released so that the second tissue engaging surface 14 is moves downwardly. In this way, the second tissue engaging surface 14 retracts away from the tissue 2, such that the floor of the base retracts, similar to the first tissue engaging surface 20 of the previous embodiments retracting towards and away from the tissue sample 2. Other than these differences noted, the embodiment shown in FIGS. 8A and 8B has the same configuration and tracks the same structure as discussed above.

Figure 9:
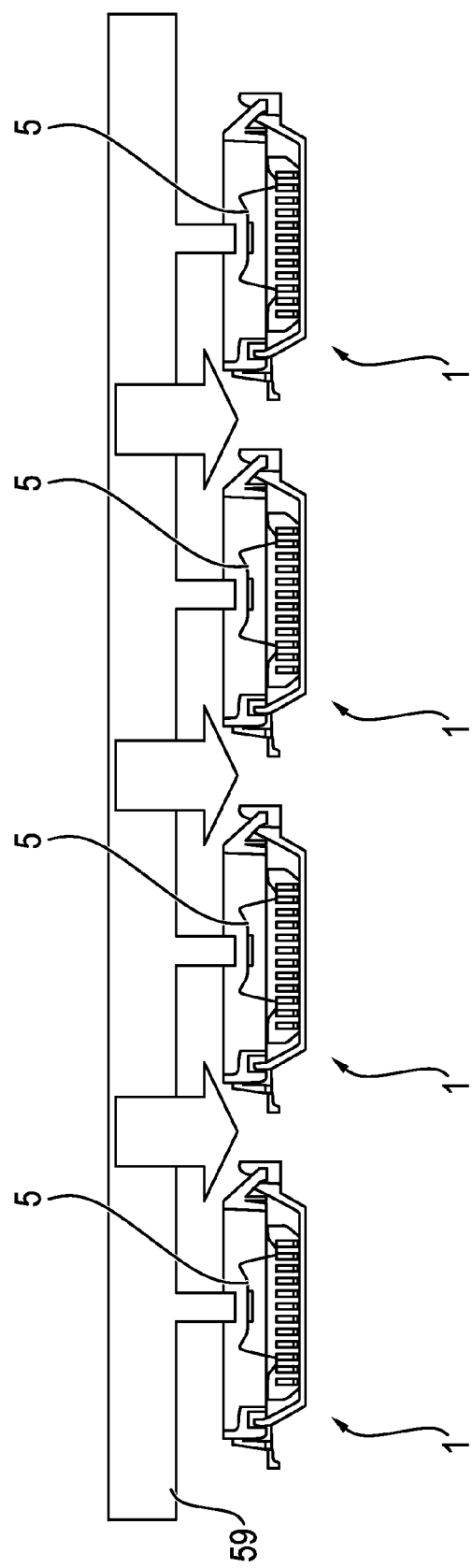
FIG. 9 illustrates a plurality of tissue retaining members and retracting members.

FIG. 9 shows an alternate embodiment in which a plurality of tissue cassettes are provided and a single plate 59 is used to retract the retaining members 18 of the tissue cassettes at the same time.

Figure 10:
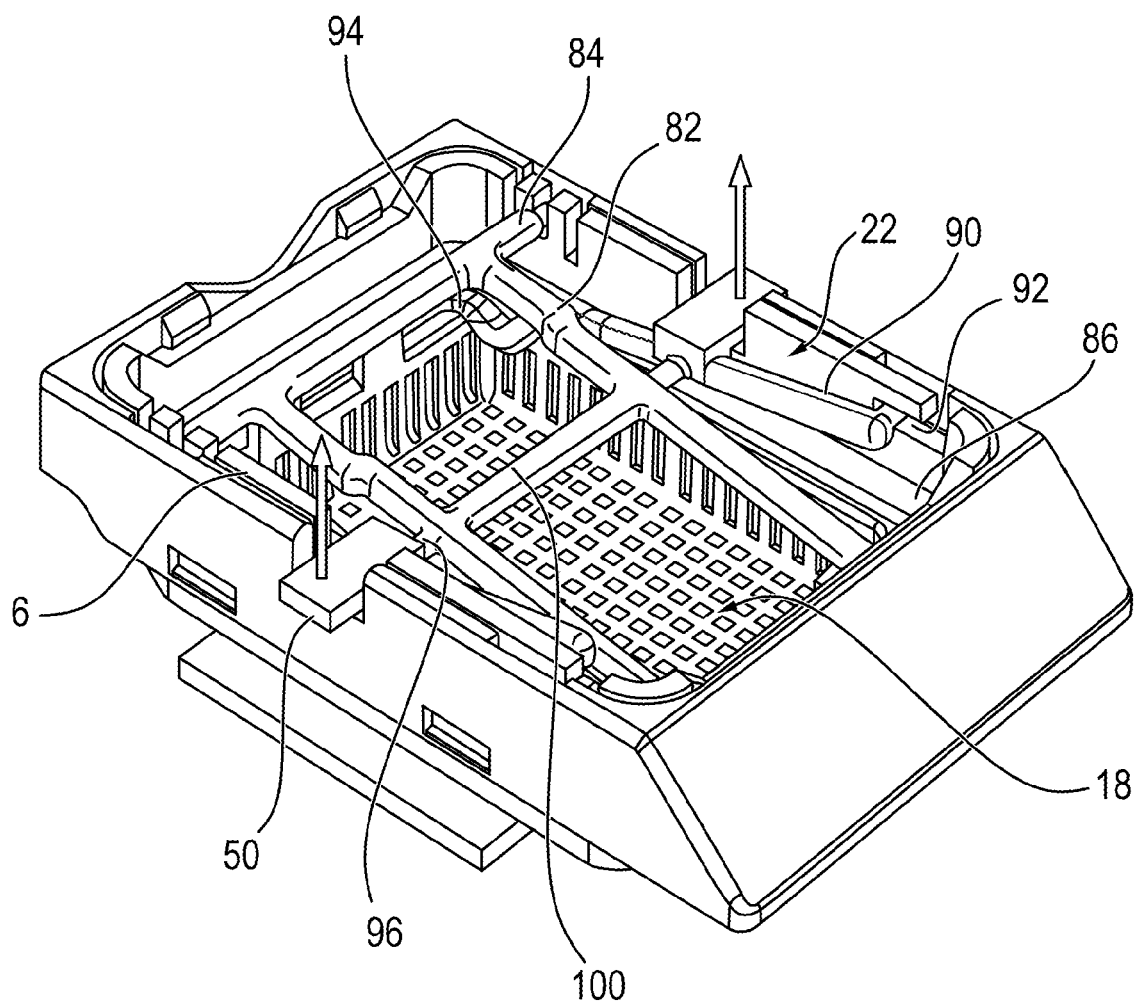
FIG. 10 illustrates the tissue cassette according to other embodiments in an assembled state.

FIG. 10 illustrates an alternative design for the biasing elements 22 as well as a related alternative design for the retracting member. A similar biasing element design is discussed in a related application U.S. Patent Application No. 61/798,728, title "Tissue Cassette with Biasing Element" referenced above.

As shown in FIG. 10, the biasing element 22 includes two angled members 82, 90. One end of the first angled member 82 is fixed to the retaining member 6 at a fixed point 84 and angles downward from the fixed point 84. The opposite end of the first angled member 82 attaches to the retaining element 18 at a first moving point 86. One end of the second angled member 90 is slidably received in a notch 92 of the retaining member 6 in a direction parallel to the second tissue engaging surface 14. The opposite end of the second angled member 90 is attached to the retaining element 18 at a second moving point 94. The first angled member 82 and the second angled member 90 are angled such that the members cross substantially in the center of each member at a hinge point 96 where they are connected to a cross member 100, as shown in FIG. 10.

Similar to the example of the biasing element 22 described above the biasing element 22 shown in FIG. 10 can be retracted by a retracting member 5, such as tabs 50 connected to the cross member 100. As shown in FIG. 10, tabs 50 extend out from the biasing element 22 and hang over the frame. Thus, the tabs 50 can be pulled or pushed in an upwardly direction to compress the biasing element 22 and retract the retaining element 18. The tabs 50 can be placed anywhere on the retaining member 6 connected to the retaining element 18, similar to the embodiment described with respect to FIG. 5C.

Alternatively, a tool 57 could be provided to rotate the second angled member to slide along the notch 92 to retract the retaining element 18.

In another exemplary embodiment of the tissue cassette 1, the retracting member 5 may be formed from a shaped memory polymer. In certain examples of this embodiment, the shape memory polymer deforms and retracts the retaining element 18 when exposed to a thermal change, such as an increase or decrease in temperature. For example, the retracting member 5 may be part of the biasing member 22 and the biasing member 22 may be a shaped memory polymer such that the biasing element 22 deforms and compresses when exposed to a first external stimulus, for example, a thermal change, and return to their original (permanent) shape when exposed to a second external stimulus, such as a further thermal change. In other exemplary embodiments, the shape memory polymer may deform when exposed to radiation, such as electromagnetic radiation, infrared radiation, or ultraviolet radiation. Non-limiting examples of shape memory polymers include linear block copolymers and other thermoplastic copolymers but may include metallic alloys, ceramics and gels.

The previous description of the non-limiting embodiments is provided to enable one skilled in the art to make and use the present invention. Moreover, various modifications to these embodiments will be readily apparent to those skilled in the art, and the generic principles and specific examples defined herein may be applied to other embodiments without the use of inventive faculty. Therefore, the present invention is not intended to be limited to the embodiments described herein, but is to be accorded the widest possible scope as defined by the recitations of the claims and equivalents thereof.

What is claimed is:

1. An apparatus for holding a tissue sample comprising,
   a retaining member having an first tissue engaging surface and at least one biasing element, the first tissue engaging surface being moveably attached to the retaining member by said biasing element;
   a base comprising a second tissue engaging surface and configured to engage the retaining member to form an interior area with the first and second tissue engaging surfaces facing each other;
   the at least one biasing element configured to urge the first tissue engaging surface toward the second tissue engaging surface to retain the tissue sample therebetween in the interior area, and
   a retracting member connected to the retaining member and configured to retract the first tissue engaging surface and compress the biasing element to form a gap between the tissue sample and one of the first tissue engaging surface and the second tissue engaging surface.

2. The apparatus according to claim 1, wherein the retracting member comprises a lever member, wherein the retracting member is configured to receive a force to retract the first tissue engaging surface.

3. The apparatus according to claim 1, wherein the retracting member comprises a ferromagnetic member connected with the first tissue engaging surface and configured to retract the first tissue engaging surface to form a gap between the tissue sample and the one of the first tissue engaging surface and the second tissue engaging surface as a result of a magnetic field being applied to the apparatus.

4. The apparatus according to claim 1, wherein the retracting member comprises a portion of the retaining member formed from a shaped memory polymer.

5. The apparatus according to claim 4, wherein the shaped memory polymer is configured to deform and retract the first tissue engaging surface when exposed to thermal change.

6. The apparatus according to claim 5, wherein the thermal change is an increase in temperature.

7. The apparatus according to claim 5, wherein the thermal change is a decrease in temperature.

8. The apparatus according to claim 4, wherein the shaped memory polymer is configured to deform and retract the first tissue engaging surface when exposed to electromagnetic radiation.

9. The apparatus according to claim 4, wherein the retracting member is configured to deform when exposed to infrared (IR) radiation.

10. The apparatus according to claim 4, wherein the retracting member is configured to deform when exposed to ultraviolet (UV) radiation.

11. The apparatus according to claim 1, wherein at least one dead stop is provided on at least one of the retaining member and the base or frame to prevent the retracting member from retracting the first tissue engaging surface more than a predefined retraction distance.

12. The apparatus according to claim 1, wherein the retaining member comprises a frame,
   wherein the frame is configured to receive and surround the retaining member.

13. The apparatus according to claim 12, wherein an ID tag is attached to the frame.

14. The apparatus according to claim 13, wherein the ID tag comprises a computer readable ID tag.

15. The apparatus according to claim 14, wherein the computer readable ID tag comprises at least one of a readable writable RFID tag a two-dimensional barcode and a three-dimensional barcode.

16. The apparatus according to claim 14, wherein the computer readable ID tag contains information unique to the tissue sample.

17. The apparatus according to claim 16, wherein the information unique to the tissue sample includes one or more of patient identification information, sample collection site location information, collection temperature, collection time, and other collection conditions.

18. The apparatus according to claim 1, wherein the first tissue engaging surface comprises a perforated surface having a plurality of holes formed therethrough.

19. The apparatus according to claim 1, wherein the retaining member comprises at least two biasing elements.

20. The apparatus according to claim 1, wherein the second tissue engaging surface comprises a solid surface.

21. The apparatus according to claim 20, wherein the acetal copolymer is DELRIN 900.

22. The apparatus according to claim 1, wherein the retaining member is formed of an acetal copolymer.

23. The apparatus according to claim 1, wherein the base is formed of polypropylene.

24. The apparatus according to claim 1, wherein the retaining member is formed of polypropylene.

25. The apparatus according to claim 1, wherein the retaining member comprises a sealing member that forms a liquid seal between the retaining member and the base to prevent liquid from leaking between the retaining member and the base.

26. An apparatus for holding a tissue sample comprising,
   a retaining member having a first tissue engaging surface;
   a base having a second tissue engaging surface;
   at least one biasing element which moveably attaches at least one of the retaining member to the first tissue engaging surface and the base to the second tissue engaging surface; and
   a retracting member connected to at least one of the retaining member or the base and configured,
   wherein the base and the retaining member are configured to engage each other to form an interior area with the first and second tissue engaging surfaces facing each other, and
   the at least one biasing element urges at least one of the first tissue engaging surface and the second tissue engaging surface to retain the tissue sample therebetween in the interior area, and
   the retracting member retracts at least one of the first tissue engaging surface and the second tissue engaging surface and compresses the biasing element.

27. An method for holding a tissue sample comprising,
   placing the tissue sample in a retaining member having an first tissue engaging surface and at least one biasing element such that the first tissue engaging surface is moveably attached to the retaining member by said biasing element, and a base comprising a second tissue engaging surface;
   engaging the base to the retaining member to form an interior area with the first and second tissue engaging surfaces facing each other;
   urging the first tissue engaging surface toward the second tissue engaging surface to retain the tissue sample therebetween in the interior area;
   processing the tissue sample with a fixing agent;
   filling the base with a paraffin to form a first layer of paraffin adjacent to the base and a second layer of paraffin above the first layer of paraffin,
   holding the base against a chilling surface to cool the first layer of paraffin,
   retracting the first tissue engaging surface by compressing the biasing element to form a gap between the tissue sample and one of the first tissue engaging surface and the second tissue engaging surface;
   holding the first tissue engaging surface away from the second tissue engaging surface until the second layer of paraffin cools;
   removing the base from the retaining element to expose the tissue sample embedded in the paraffin.

* * * * *